United States Patent
Hatakeyama

(10) Patent No.: US 8,346,352 B2
(45) Date of Patent: Jan. 1, 2013

(54) SLEEPINESS JUDGING DEVICE

(75) Inventor: Yoshiyuki Hatakeyama, Susono (JP)

(73) Assignee: Toyota Jidosha Kabushiki Kaisha, Toyota (JP)

( * ) Notice: Subject to any disclaimer, the term of this patent is extended or adjusted under 35 U.S.C. 154(b) by 273 days.

(21) Appl. No.: 12/666,452

(22) PCT Filed: Aug. 1, 2008

(86) PCT No.: PCT/JP2008/063892
§ 371 (c)(1),
(2), (4) Date: Dec. 23, 2009

(87) PCT Pub. No.: WO2009/020074
PCT Pub. Date: Feb. 12, 2009

(65) Prior Publication Data
US 2010/0234747 A1    Sep. 16, 2010

(30) Foreign Application Priority Data
Aug. 6, 2007    (JP) ................................. 2007-204288

(51) Int. Cl.
*A61B 5/0402*    (2006.01)
(52) U.S. Cl. ...................................................... 600/519
(58) Field of Classification Search .................. 600/513, 600/519, 520
See application file for complete search history.

(56) References Cited

U.S. PATENT DOCUMENTS

| | | | |
|---|---|---|---|
| 6,126,595 A | 10/2000 | Amano et al. | |
| 6,890,304 B1 | 5/2005 | Amano et al. | |

FOREIGN PATENT DOCUMENTS

| | | |
|---|---|---|
| JP | A-4-348759 | 12/1992 |
| JP | A-6-270711 | 9/1994 |
| JP | A-08-280637 | 10/1996 |
| JP | A-8-299443 | 11/1996 |
| JP | A-2006-158733 | 6/2006 |
| JP | A-2007-6970 | 1/2007 |
| JP | A-2007-140975 | 6/2007 |
| JP | A-2007-229218 | 9/2007 |
| KR | 1020060030880 A | 4/2006 |
| KR | 100718941 B1 | 5/2007 |

OTHER PUBLICATIONS

Machine Translation of KR 10/2005/0117630, published May 16, 2077.*
English Translation of Korean Patent No. 100718941, dated May 15, 2007, as translated by Schreiber Translations, Inc., May 2012.*
Aug. 26, 2008 International Search Report issued in International Patent Application No. PCT/JP2008/063892.

* cited by examiner

*Primary Examiner* — Scott Getzow
*Assistant Examiner* — Amanda Patton
(74) *Attorney, Agent, or Firm* — Oliff & Berridge, PLC

(57) ABSTRACT

The object is to provide a drowsiness detecting device for detecting strong drowsiness to become a dozing state. A drowsiness detecting device comprises a sympathetic parameter acquiring unit for acquiring a parameter concerning a sympathetic nerve of a subject, a parasympathetic parameter acquiring unit for acquiring a parameter concerning a parasympathetic nerve of the subject, a sympathetic increase determining unit for determining whether the sympathetic parameter is greater than a sympathetic threshold or not, and a drowsiness determining unit for determining drowsiness of the subject according to an increase/decrease relationship between the sympathetic and parasympathetic parameters when the sympathetic increase determining unit determines that the sympathetic parameter is greater than the sympathetic threshold.

4 Claims, 19 Drawing Sheets

Fig.17
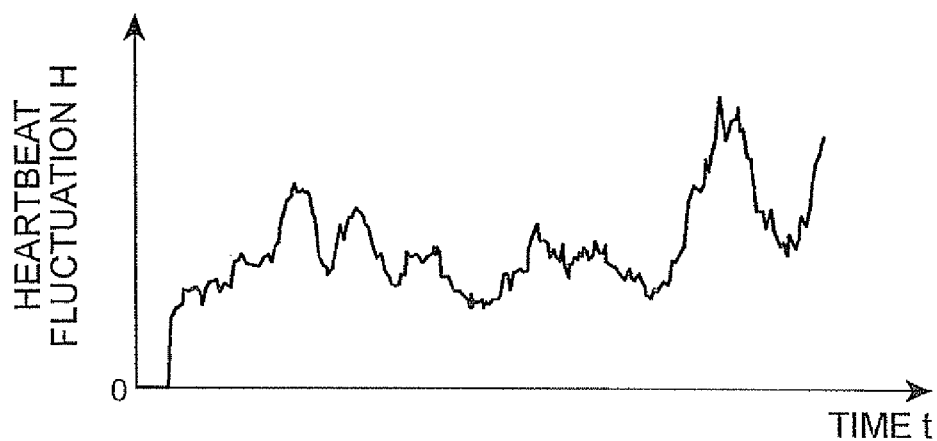
(a)
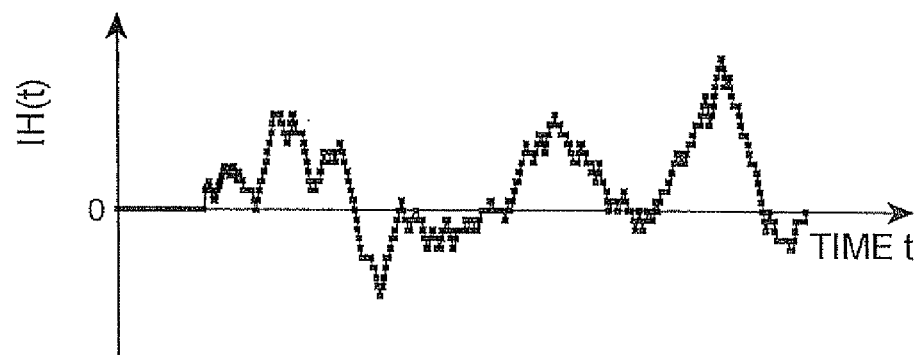
(b)
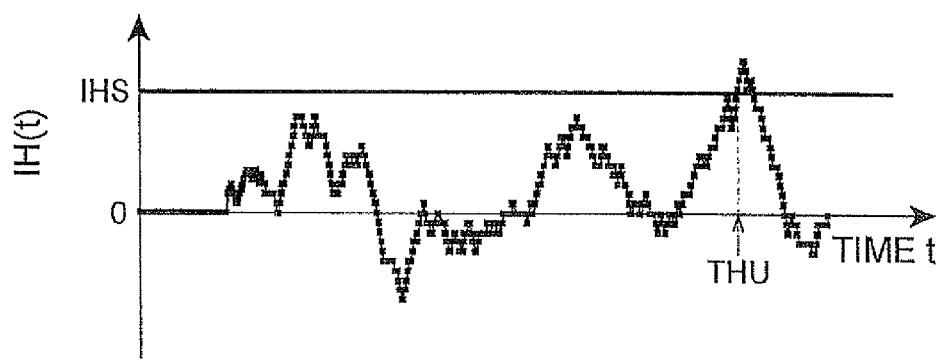
(c)

Fig.19

| DROWSINESS LEVEL | Sens VALUE RANGE |
|---|---|
| D0 | $0 \leq Sens < 1$ |
| D1 | $1 \leq Sens < 2$ |
| D2 | $2 \leq Sens < 3$ |
| D3 | $3 \leq Sens < 4$ |
| D4 | $4 \leq Sens < 5$ |

Sens: SENSORY EVALUATION AVERAGE VALUE

SLEEPINESS JUDGING DEVICE

TECHNICAL FIELD

The present invention relates to a drowsiness determining device which determines drowsiness according to sympathetic and parasympathetic activities.

BACKGROUND ART

Devices for determining drowsiness (degree of awakening) of a driver of a vehicle have been developed in order for the driver to drive safely. An example of the drowsiness determining devices extracts a characteristic amount changing according to drowsiness from heartbeats and blinks, for example, and determines very strong drowsiness (a dozing state or a state immediately before the dozing state). When such very strong drowsiness is determined, its drowsiness level is such that an influence (e.g., faltering) appears in a driving operation, whereby the determination timing is late. Hence, the device disclosed in Patent Literature 1 determines weak drowsiness according to a heartbeat fluctuation low frequency component which is correlated with a sympathetic activity, and provides a stimulus when the weak drowsiness is determined.

Patent Literature 1: Japanese Patent Application No. 2007-140975
Patent Literature 2: Japanese Patent Application Laid-Open No. 2007-6970
Patent Literature 3: Japanese Patent Application Laid-Open No. 6-270711

SUMMARY OF INVENTION

Technical Problem

There are cases where the degree of awakening rises after weak drowsiness, so that the dozing state is avoided. Even when shifting from the weak drowsiness to the dozing state, how long it takes for the weak drowsiness to shift to the dozing state is uncertain, and the time varies among people. Therefore, strong drowsiness which certainly shifts to the dozing state and takes only a short time for the shift must be determined (several to ten-odd minutes before the occurrence of the dozing state). However, the conventional drowsiness determining devices have failed to determine the strong drowsiness.

It is therefore an object of the present invention to provide a drowsiness determining device which determines the strong drowsiness to become the dozing state.

Solution to Problem

The drowsiness determining device in accordance with the present invention comprises a sympathetic parameter acquiring unit for acquiring a parameter concerning a sympathetic nerve of a subject, a parasympathetic parameter acquiring unit for acquiring a parameter concerning a parasympathetic nerve of the subject, a sympathetic increase determining unit for determining whether the sympathetic parameter acquired by the sympathetic parameter acquiring unit is greater than a sympathetic threshold or not, and a drowsiness determining unit for determining drowsiness of the subject according to an increase/decrease relationship between the sympathetic parameter acquired by the sympathetic parameter acquiring unit and the parasympathetic parameter acquired by the parasympathetic parameter acquiring unit when the sympathetic increase determining unit determines that the sympathetic parameter is greater than the sympathetic threshold.

In this drowsiness determining device, the sympathetic parameter acquiring unit acquires a sympathetic parameter of a subject, while the parasympathetic parameter acquiring unit acquires a parasympathetic parameter of the subject. The sympathetic parameter is any of various parameters indicating an activity of a sympathetic nerve; the greater the parameter is, the brisker, the activity of the sympathetic nerve becomes. The parasympathetic parameter is any of various parameters indicating an activity of a parasympathetic nerve; the greater the parameter is, the brisker the activity of the parasympathetic nerve becomes. In the drowsiness determining device, the sympathetic increase determining unit determines whether the sympathetic parameter of the subject is greater than a sympathetic threshold or not. The sympathetic parameter is a threshold for determining a state where the sympathetic activity is brisk (a weakly drowsy state acting against drowsiness). When becoming the dozing state, a weakly drowsy state, a strongly drowsy state, and the dozing state occur in this order. Therefore, in the drowsiness determining device, the drowsiness determining unit determines the drowsiness of the subject (strong drowsiness before the dozing state in particular) according to an increase/decrease relationship between the sympathetic and parasympathetic parameters after the sympathetic parameter becomes greater than the sympathetic threshold. Thus, the drowsiness determining device can determine the strong drowsiness to become the dozing state with a high accuracy from the increase/decrease relationship between the sympathetic and parasympathetic activities after the sympathetic activity becomes brisk (after the weakly drowsy state), thus making it possible to predict an occurrence of the dozing state.

Preferably, in the drowsiness determining device in accordance with the present invention, the sympathetic increase determining unit determines that the sympathetic parameter is greater than the sympathetic threshold when a duration during which the sympathetic parameter acquired by the sympathetic parameter acquiring unit is greater than the sympathetic threshold is longer than a time threshold.

In this drowsiness determining device, the sympathetic increase determining unit determines whether a duration during which the sympathetic parameter acquired by the sympathetic parameter acquiring unit is greater than the sympathetic threshold is longer than a time threshold or not, and determines that the sympathetic parameter is greater than the sympathetic threshold when the duration is longer than the time threshold. The time threshold is a threshold for determining that the sympathetic activity is certainly brisk (the weak drowsiness continues). Thus, by determining a brisk state of the sympathetic activity by introducing the concept of time as well, the drowsiness determining device can determine a state where the sympathetic activity is brisk (that the weakly drowsy state continues) with a high accuracy, thereby making it possible to determine the strong drowsiness with a high accuracy.

In the drowsiness determining device in accordance with the present invention, the parasympathetic parameter acquiring unit acquires the parasympathetic parameter according to an increase/decrease direction of a heartbeat fluctuation high frequency component.

The heartbeat fluctuation high frequency component is correlated with the parasympathetic nerve; the greater the heartbeat fluctuation high frequency component is, the brisker the activity of the parasympathetic nerve becomes. Therefore, in this drowsiness determining device, the parasympathetic parameter acquiring unit determines whether the heartbeat fluctuation high frequency component increases or decreases, and acquires the parasympathetic parameter according to the increase/decrease direction. Thus, simply taking only the increase/decrease of the heartbeat fluctuation high frequency component, the drowsiness determining device can absorb individual differences, thereby making it possible to determine the strong drowsiness with a higher accuracy.

The drowsiness determining device in accordance with the present invention may further comprise a parasympathetic increase determining unit for determining whether the parasympathetic parameter acquired by the parasympathetic parameter acquiring unit is greater than a parasympathetic threshold or not, wherein the drowsiness determining unit determines that the subject is in a strongly drowsy state when the parasympathetic increase determining unit determines that the parasympathetic parameter is greater than the parasympathetic threshold after the sympathetic increase determining unit determines that the sympathetic parameter is smaller than the sympathetic threshold in a case where the sympathetic increase determining unit determines that the sympathetic parameter is greater than the sympathetic threshold.

In this drowsiness determining device, the parasympathetic increase determining unit determines whether the parasympathetic parameter is greater than a parasympathetic threshold or not. The parasympathetic threshold is a threshold for determining whether or not the parasympathetic activity is so brisk that the weakly drowsy state shifts to the strongly drowsy state. In the drowsiness determining device, the drowsiness determining unit determines that the subject is in a strongly drowsy state when the parasympathetic increase determining unit determines that the parasympathetic parameter has become greater than the parasympathetic threshold after the sympathetic parameter became smaller than the sympathetic threshold after having become greater than the sympathetic threshold. Thus, by determining that the parasympathetic activity has become brisk after a brisk state of the sympathetic activity was subdued, the drowsiness determining device can determine the strong drowsiness with a high accuracy.

The drowsiness determining device in accordance with the present invention may further comprise a parasympathetic increase determining unit for determining whether the parasympathetic parameter acquired by the parasympathetic parameter acquiring unit is greater than a parasympathetic threshold or not, wherein the drowsiness determining unit determines that the subject is in a strongly drowsy state when the parasympathetic increase determining unit determines that the parasympathetic parameter is greater than the parasympathetic threshold while the sympathetic increase determining unit keeps determining that the sympathetic parameter is greater than the sympathetic threshold in a case where the sympathetic increase determining unit determines that the sympathetic parameter is greater than the sympathetic threshold.

In this drowsiness determining device, the parasympathetic increase determining unit determines whether the parasympathetic parameter is greater than a parasympathetic threshold or not. In the drowsiness determining device, the drowsiness determining unit determines that the subject is in a strongly drowsy state when the parasympathetic parameter has become greater than the parasympathetic threshold while the sympathetic parameter keeps its greater state after having become greater than the sympathetic threshold. Thus, by determining that the parasympathetic activity becomes brisk while the sympathetic activity keeps its brisk state, the drowsiness determining device can determine the strong drowsiness with a high accuracy.

Advantageous Effects of Invention

By determining the increase/decrease relationship between the sympathetic and parasympathetic activities after the sympathetic activity becomes brisk, the present invention can determine the strong drowsiness to become the dozing state with a high accuracy.

BRIEF DESCRIPTION OF DRAWINGS

FIG. 17 is an example of evaluation tests for the dozing occurrence predicting device, in which (a) is a time series of the heartbeat fluctuation H, (b) is a time series of a sign integral IH(t), and (c) is the time series of sign integral IH(t) with a parasympathetic activity briskness determining threshold IHS;

FIG. 19 is a table showing criteria for determining the drowsiness levels by the sensory evaluations.

REFERENCE SIGNS LIST

Figure 1:
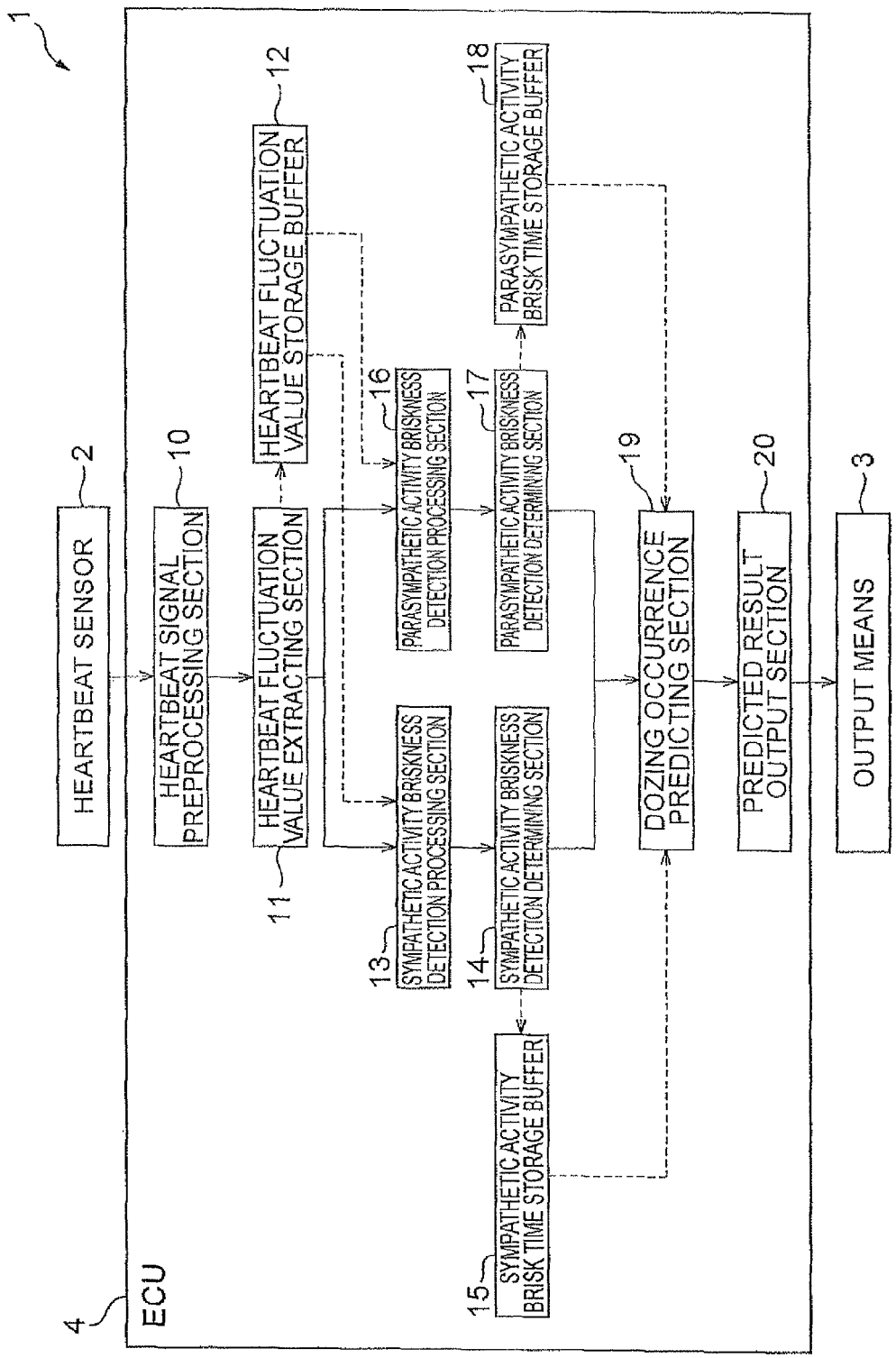
FIG. 1 is a block diagram showing an overall structure of a dozing occurrence predicting device in accordance with an embodiment of the present invention.

1 . . . drowsiness occurrence predicting device; 2 . . . heartbeat sensor; 3 . . . output unit; 4 . . . ECU; 10 . . . heartbeat signal preprocessing section; 11 . . . heartbeat fluctuation value extracting section; 12 . . . heartbeat fluctuation value storage buffer; 13 . . . sympathetic activity briskness detection processing section; 14 . . . sympathetic activity briskness detection determining section; 15 . . . sympathetic activity brisk time storage buffer; 16 . . . parasympathetic activity briskness detection processing section; 17 . . . parasympathetic activity briskness detection determining section; 18 . . . parasympathetic activity brisk time storage buffer; 19 . . . drowsiness occurrence predicting section; 20 . . . predicted result output section

DESCRIPTION OF EMBODIMENTS

In the following, an embodiment of the present invention will be explained with reference to the drawings.

This embodiment employs the drowsiness determining device in accordance with the present invention as a dozing occurrence predicting device which is mounted to a vehicle and predicts an occurrence of a dozing state of a driver. The dozing occurrence predicting device in accordance with this embodiment determines a strongly drowsy state to become a dozing state (a state of several to ten-odd minutes before the occurrence of the dozing state) according to a heartbeat fluctuation and, when the strongly drowsy state is detected, notifies the result of determination.

Before specifically explaining the dozing occurrence predicting device in accordance with this embodiment, a method of determining a strongly drowsy state will be explained. First, terms used in this embodiment will be explained. Heartbeat fluctuations are fluctuations of heartbeats in a heartbeat period of about 0.01 Hz to about 0.5 Hz. The heartbeat fluctuation low frequency component (hereinafter referred to as "heartbeat fluctuation L") is a heartbeat fluctuation component power around the heartbeat period of 0.1 Hz. The heartbeat fluctuation high frequency component (hereinafter referred to as "heartbeat fluctuation H") is a heartbeat fluctuation component power around the heartbeat period of 0.3 Hz. The heartbeat fluctuation low component/high component (hereinafter referred to as "heartbeat fluctuation L/H") is the ratio of the heartbeat fluctuation L to the heartbeat fluctuation H.

The inventor statistically analyzed heartbeat data (heartbeat fluctuation L, heartbeat fluctuation H, and heartbeat fluctuation L/H), sensory evaluations of drowsy states, and the like obtained by experiments with respect to a number of subjects and so forth and, as a result, has found a change characteristic of heartbeat fluctuations when attaining a strongly drowsy state. This change characteristic has two-stage conditions. The first is a condition under which the heartbeat fluctuation L/H or heartbeat fluctuation L increases. The second is a condition under which the heartbeat fluctuation H increases after the increased heartbeat fluctuation L/H or heartbeat fluctuation L decreases, or a condition under which the heartbeat fluctuation H increases while the heartbeat fluctuation L/H or heartbeat fluctuation L keeps its increased state.

The following relationship has been known to exist between heartbeat fluctuations and autonomic nerves (sympathetic and parasympathetic nerves) in general. The heartbeat fluctuation L changes under the influence of (i.e., is correlated with) sympathetic and parasympathetic activities, so as to increase its component power as each nerve activity becomes brisker. The heartbeat fluctuation H changes under the influence of the parasympathetic activity, so as to increase its component power as the parasympathetic activity becomes brisker. The heartbeat fluctuation L/H changes under the influence of the sympathetic activity, so as to increase its component power as the sympathetic activity becomes brisker.

Therefore, the following is an activity characteristic of the autonomic nerves (sympathetic and parasympathetic nerves) when getting into the strongly drowsy state. This activity characteristic also has two-stage conditions. The first is a condition under which the sympathetic activity becomes brisk. The second is a condition under which the parasympathetic activity becomes brisk after the brisk state of the sympathetic activity is subdued or a condition under which the parasympathetic activity becomes brisk while the sympathetic activity keeps its brisk state. That is, when the sympathetic activity is brisk, it is a state acting against drowsiness, where weak drowsiness occurs. Thereafter, when the parasympathetic activity becomes brisk, it seems to fail to stand against drowsiness, so that the weak drowsiness shifts to strong drowsiness. Once the strong drowsiness occurs, it will become a dozing state after several to ten-odd minutes.

Thus, the present invention determines the strong drowsiness (predicts the occurrence of dozing) by detecting a brisk state of the sympathetic activity and then detecting a brisk state of the parasympathetic activity after the brisk state of the sympathetic activity is subdued or while the sympathetic activity keeps its brisk state. Further, when detecting the brisk state of the sympathetic activity, the absolute value is detected for the heartbeat fluctuation L or L/H by using preset sympathetic threshold and duration threshold. When detecting the brisk state of the parasympathetic activity, the absolute value is detected for a time integral of the increase/decrease direction (sign) of the heartbeat fluctuation H by using a preset parasympathetic threshold. The absolute value is detected with the same threshold for all the people instead of respective thresholds set for individuals (i.e., not detected from relative changes in individual heartbeat fluctuation values).

First, with reference to FIG. 1, the structure of a dozing occurrence predicting device 1 in accordance with this embodiment will be explained. FIG. 1 is a block diagram showing the overall structure of the dozing occurrence predicting device 1 in accordance with this embodiment.

The dozing occurrence predicting device 1 extracts heartbeat fluctuation values (heartbeat fluctuations L, H, and L/H) from heartbeat indexes detected from a driver. Then, according to the heartbeat fluctuation values, the dozing occurrence predicting device 1 detects a brisk state of the sympathetic activity and a brisk state of the parasympathetic activity after the brisk state of the sympathetic activity is subdued, thereby determining whether a strongly drowsy state is attained or not.

To this aim, the dozing occurrence predicting device 1 comprises a heartbeat sensor 2, an output means 3, and an ECU (Electronic Control Unit) 4, while a heartbeat signal preprocessing section 10, a heartbeat fluctuation value extracting section 11, a heartbeat fluctuation value storage buffer 12, a sympathetic activity briskness detection processing section 13, a sympathetic activity briskness detection determining section 14, a sympathetic activity brisk time storage buffer 15, a parasympathetic activity briskness detection processing section 16, a sympathetic activity briskness detection determining section 17, a parasympathetic activity brisk time storage buffer 18, a dozing occurrence predicting section 19, and a predicted result output section 20 are constructed in the ECU 4.

In this embodiment, the heartbeat sensor 2 and heartbeat fluctuation value extracting section 11 corresponds to the sympathetic parameter acquiring unit recited in the claims; the heartbeat sensor 2, heartbeat fluctuation value extracting section 11, and parasympathetic activity briskness detection processing section 16 correspond to the parasympathetic parameter acquiring unit recited in the claims; the sympathetic activity briskness detection processing section 13 and sympathetic activity briskness detection determining section 14 correspond to the sympathetic increase determining unit recited in the claims; the parasympathetic activity briskness detection processing section 16 and parasympathetic activity briskness detection determining section 17 correspond to the parasympathetic increase determining unit recited in the claims; and the dozing occurrence predicting section 19 corresponds to the drowsiness determining unit recited in the claims.

The heartbeat sensor 2 is a potentiometric heartbeat sensor for detecting a pulsed voltage (cardiac potential) occurring when cardiac muscle contracts. The heartbeat sensor 2 detects the cardiac potential from an electrode attached to a steering wheel of the vehicle or the like, for example. The heartbeat sensor 2 detects the cardiac potential and outputs the detected cardiac potential as a heartbeat signal to the ECU 4. As the heartbeat sensor, not only potentiometric heartbeat sensors, but also infrared heartbeat sensors which detect the infrared reflected light quantity periodically changing in response to heartbeats, sensors for detecting the blood pressure of the driver, and the like can be used.

The output means 3 is a means for enabling an output object to notify a fact that the driver is in the strongly drowsy state or to urge the driver to take a rest. Upon receiving an output signal from the ECU 4, the output means 3 issues an output corresponding to each means. Examples of the output means 3 include those notifying by sounds (buzzers, audios, radios, and horns), those notifying by image displays (displays), those notifying by light (meter illumination and room illumination), those notifying by tactile/thermal senses (vibrators embedded in the steering wheel or seat and winds and temperature changes in air-conditioners), those notifying by scents (spraying of fragrances), and command outputs to systems. Examples of the output objects include the driver, passengers sitting anywhere other than the driver's seat, managers managing operations of commercial vehicles such as trucks and taxis, and vehicle control systems.

The ECU 4 is constituted by a CPU (Central Processing Unit), a ROM (Read Only Memory), a RAM (Random Access Memory), and the like and controls the dozing occurrence predicting device 1 as a whole. By causing the CPU to execute programs stored in the ROM, the ECU 4 constructs the processing sections 10, 11, 13, 14, 16, 17, 19, 20 and buffers 12, 16, 18 and performs processes of the processing sections 10, 11, 13, 14, 16, 17, 19, 20.

The heartbeat signal preprocessing section 10 reads the heartbeat signal from the heartbeat sensor 2 at predetermined time intervals, so as to acquire a heartbeat period (RR interval) time series from the heartbeat signal. Specifically, after subjecting the heartbeat signal to a bandpass filtering process, time-series data exceeding a threshold is cut out. Subsequently, thus cut-out time-series data is binarized, and an interval width (period) is determined by utilizing the binarized data. Then, the interval width is interpolated, so as to determine time-series data of the heartbeat period. The heartbeat signal preprocessing section 10 outputs thus acquired heartbeat period time-series data to the heartbeat fluctuation value extracting section 11.

The heartbeat fluctuation value extracting section 11 extracts time series of heartbeat fluctuations L, H, and L/H from the heartbeat period time-series data acquired by the heartbeat preprocessing section 10. Specifically, first, the heartbeat period time-series data is subjected to an FFT process, so as to acquire a power spectrum which is a heartbeat fluctuation frequency component. Subsequently, a low frequency component (around 0.1 Hz) and a high frequency component (around 0.3 Hz) are designated for this power spectrum, and the power spectrum of each frequency band is integrated. Further, the integral of the heartbeat fluctuation low frequency component is divided by the integral of the heartbeat fluctuation high frequency component. This processing is performed repeatedly, so as to acquire time-series data of amplitude spectral power of the heartbeat fluctuation low frequency component (heartbeat fluctuation L), time-series data of amplitude spectral power of the heartbeat fluctuation high frequency component (heartbeat fluctuation H), and time-series data of amplitude spectral power of the heartbeat fluctuation low frequency component/heartbeat fluctuation high frequency component (heartbeat fluctuation L/H). The heartbeat fluctuation value extracting section 11 stores the acquired heartbeat fluctuations L, H, and L/H into the heartbeat fluctuation value storage buffer 12 at predetermined time intervals.

The heartbeat fluctuation value storage buffer 12 is a buffer for storing the time-series data of heartbeat fluctuations L, H, and L/H extracted by the heartbeat fluctuation value extracting section 11. The stored time-series data are data extracted during a fixed period from the past to the present. This fixed period is about several to ten-odd minutes.

Figure 13:
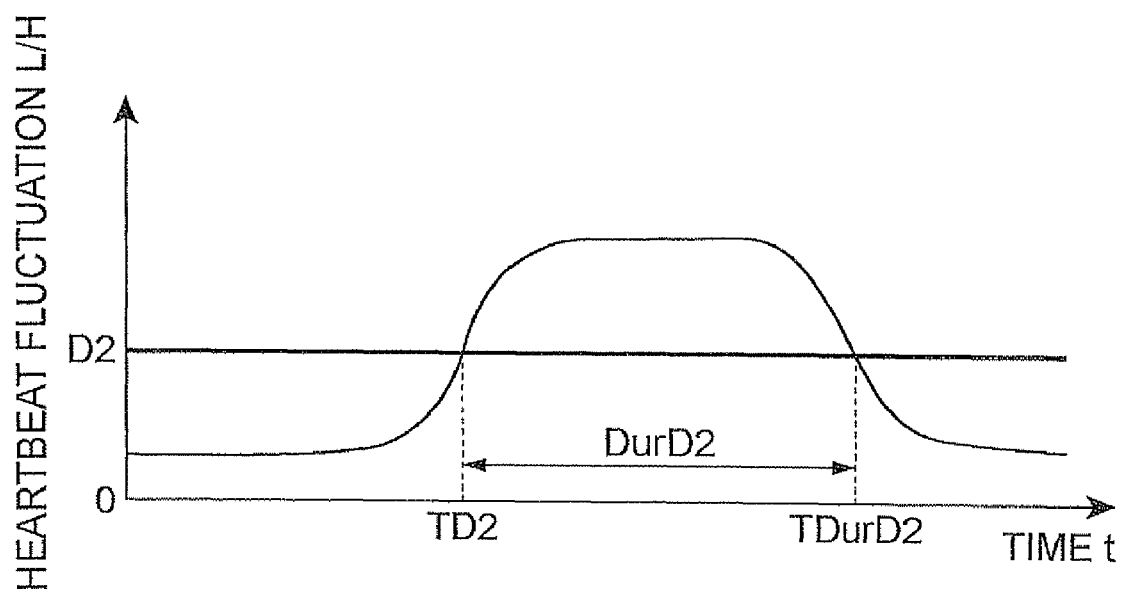
FIG. 13 is a schematic diagram for explaining a sympathetic activity briskness detecting process and a parasympathetic activity briskness detecting process.

The sympathetic activity briskness detection processing section 13 determines a brisk state of the sympathetic activity (state where the heartbeat fluctuation L or L/H has increased) by using the time-series data of heartbeat fluctuation L or L/H stored in the heartbeat fluctuation value storage buffer 12. Referring to FIG. 13, a case of detection using the heartbeat fluctuation L/H will be explained specifically. At predetermined time intervals, it is determined whether the heartbeat fluctuation L/H exceeds a sympathetic activity briskness determining threshold D2 or not. The sympathetic activity briskness determining threshold D2 is a threshold for determining a brisk state of the sympathetic activity (weakly drowsy state acting against drowsiness). When the heartbeat fluctuation L/H exceeds the sympathetic activity briskness determining threshold D2, it is determined at fixed time intervals whether the heartbeat fluctuation L/H fails to exceed the sympathetic activity briskness determining threshold D2 or not, while counting the elapsed time from the time TD2 at which the heartbeat fluctuation L/H exceeds the sympathetic activity briskness determining threshold D2. When the heartbeat fluctuation L/H becomes the sympathetic activity briskness determining threshold D2 or lower, the time TDurD2 at which the heartbeat fluctuation L/H becomes the sympathetic activity briskness determining threshold D2 is stored together with the duration DurD2 (=TDurD2−TD2) during which the time is counted.

A method for setting the sympathetic activity briskness determining threshold D2 will now be explained. An example is a method which acquires a correlation between drowsiness, which is quantified by another method, and the heartbeat fluctuation L or L/H. Known as a method for quantifying drowsiness is one which evaluates a drowsiness level from a face image (see "Human Sensory Measurement Manual, Vol. 1", p. 146, Research Institute of Human Engineering for Quality Life). By utilizing such a method, data obtained by experiments with respect to a number of subjects and the like are statistically analyzed, whereby the sympathetic activity briskness determining threshold D2 is preset. The sympathetic activity briskness determining threshold D2 is set for the heartbeat fluctuation L in the case of determination with the heartbeat fluctuation L, while the sympathetic activity briskness determining threshold D2 is set for the heartbeat fluctuation L/H in the case of determination with the heartbeat fluctuation L/H.

Using the duration DurD2 derived by the sympathetic activity briskness detection processing part 13, the sympathetic activity briskness detection determining section 14 determines whether the brisk state of the sympathetic activity is enough to predict the dozing state or not (whether the increased state of heartbeat fluctuation L or L/H is sufficiently kept or not). A case of detection with the heartbeat fluctuation L/H will now be explained specifically with reference to FIG. 13. It is determined whether the duration DurD2 during which the heartbeat fluctuation L/H surpasses the sympathetic activity briskness determining threshold D2 exceeds a duration threshold ST or not. The duration threshold ST is a threshold for determining that the brisk state of the sympathetic activity is kept sufficiently (i.e., the weakly drowsy state is kept sufficiently). The duration threshold ST, which is preset by statistically analyzing data obtained by experiments with respect to a number of subjects and the like, is about several minutes, for example. When the duration DurD2 exceeds the duration threshold ST (i.e., when the increased state of the heartbeat fluctuation L/H is kept sufficiently), the time TDurD2 at the end of the duration DurD2 (i.e., the end time of the brisk state of the sympathetic activity) is stored into the sympathetic brisk time storage buffer 15. When the weakly drowsy state continues to a certain extent, there is a high possibility of it directly shifting to strong drowsiness, thereby reaching the dozing state.

The sympathetic activity brisk time storage buffer 15 is a buffer for storing the time TDurD2 at which the brisk state of the sympathetic activity ends when the sympathetic activity briskness detection determining section 14 determines that the duration DurD2 exceeds the duration threshold ST.

Using the time-series data of heartbeat fluctuation H stored in the heartbeat fluctuation value storage buffer 12, the parasympathetic activity briskness detection processing section 16 detects a brisk state of the parasympathetic activity (derives a time integral of the increase/decrease direction (sign) of the heartbeat fluctuation H). This will be explained specifically with reference to FIG. 14. At fixed time intervals, the heartbeat fluctuation H is differentiated with respect to time, so as to generate time-series data of the derivative dH(t) of heartbeat fluctuation H. Then, at fixed time intervals, the derivative dH(t) of heartbeat fluctuation H is determined while employing 0 as a threshold, so as to be encoded such that $SH(t)=1$ when $dH(t)>0$, $SH(t)=0$ when $dH(t)=0$, and $SH(t)=-1$ when $dH(t)<0$ as shown in expression (1), whereby time-series data of derivative sign SH(t) is generated. Further, the derivative sign SH(t) is integrated with respect to time by expression (2), so as to generate time-series data of a sign integral IH(t).

[Math. 1]

In expression (1), T1 is an integration interval, an example of which is about several minutes. By encoding increases and decreases of the heartbeat fluctuation H and integrating thus encoded increasing intervals (1), fixed intervals (0), and decreasing intervals (−1), only the increase/decrease of the heartbeat fluctuation H and its increase/decrease time are simply seen, whereby states of changes in the heartbeat fluctuation H (i.e., parasympathetic activity) varying among individuals can be absorbed. For example, there are people with relatively large and small heartbeat fluctuations H even at about the same drowsiness level, and there are people increasing the heartbeat fluctuation H rapidly and gradually when drowsiness is getting stronger.

Using the time-series data of sign integral IH(t) derived by the parasympathetic activity briskness detection processing section 16, the parasympathetic activity briskness detection determining section 17 determines whether the brisk state of the parasympathetic activity is enough to predict the dozing state or not (whether the increased state of heartbeat fluctuation H is sufficiently kept or not). This will be explained specifically with reference to FIG. 15. At fixed time intervals, it is determined whether the sign integral IH(t) exceeds a parasympathetic activity briskness determining threshold IHS or not. The parasympathetic activity briskness determining threshold IHS is a threshold for determining that the brisk state of the parasympathetic activity is kept sufficiently (i.e., the weakly drowsy state has shifted to the strongly drowsy state). When the sign integral IH(t) exceeds the parasympathetic activity briskness determining threshold IHS (i.e., the increased state of heartbeat fluctuation H is kept sufficiently), the time THU at which the parasympathetic activity briskness determining threshold IHS is exceeded (i.e., the time at which the brisk state of the parasympathetic activity is started) is stored into the parasympathetic activity brisk time storage buffer 18.

A method for setting the parasympathetic activity briskness determining threshold IHS will now be explained. For the parasympathetic activity briskness determining threshold IHS, a setting method similar to that for the sympathetic activity briskness determining threshold D2 is utilized. The parasympathetic activity briskness determining threshold IHS is also determined beforehand by statistically analyzing data obtained by experiments with respect to a number of subjects and the like.

The parasympathetic activity brisk time storage buffer 18 is a buffer for storing the time THU at which the brisk state of the parasympathetic activity is started when the parasympathetic activity briskness detection determining section 17 determines that the sign integral IH(t) has exceeded the parasympathetic activity briskness determining threshold IHS.

Using the time TDurD2 stored in the sympathetic activity brisk time storage buffer 15 and the time THU stored in the parasympathetic activity brisk time storage buffer 18, the dozing occurrence predicting section 19 predicts the occurrence of dozing (i.e., determines the strongly drowsy state to become the dozing state). Specifically, it is determined whether or not the time THU at which the brisk state of the sympathetic activity ends is later than the time TDurD2 at which the brisk state of the parasympathetic activity starts while their time difference (THU−TDurD2)<a shift time threshold TSleep. The shift time threshold TSleep is a threshold for determining a time interval by which the parasympathetic activity attains the brisk state after the brisk state of the sympathetic activity is subdued, for which a time enough for weak drowsiness to shift to strong drowsiness in the process of attaining the dozing state is set. The shift time threshold TSleep, an example of which is about ten-odd minutes, is preset by statistically analyzing data obtained by experiments with respect to a number of subjects and the like. When the time THU is later than the time TDurD2 while (THU−TDurD2)<the shift time threshold TSleep (i.e., when the sympathetic activity attains the brisk state and then the parasympathetic activity attains the brisk state after the brisk state of sympathetic activity is subdued, while the shift time for the parasympathetic nerve to attain the brisk state from the state where sympathetic activity is in the brisk state is short), it is determined to be the strongly drowsy state.

When the dozing occurrence predicting section 19 determines the strongly drowsy state, the predicted result output section 20 outputs an output signal to the output means 3 in order to notify that the driver is in the strongly drowsy state or to urge the driver to take a rest.

Figure 2:
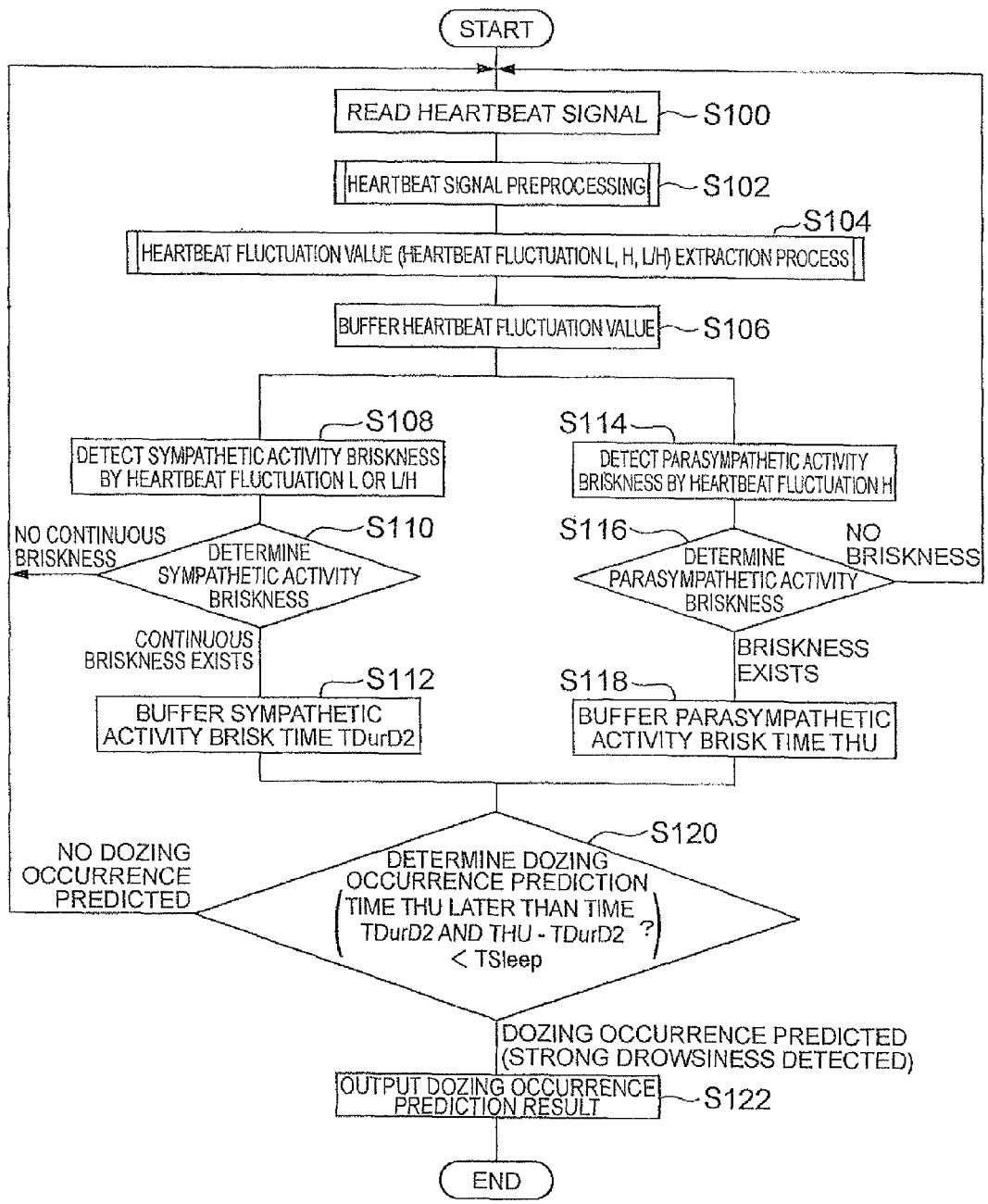
FIG. 2 is a flowchart showing a processing procedure in an ECU in FIG. 1.
Figure 3:
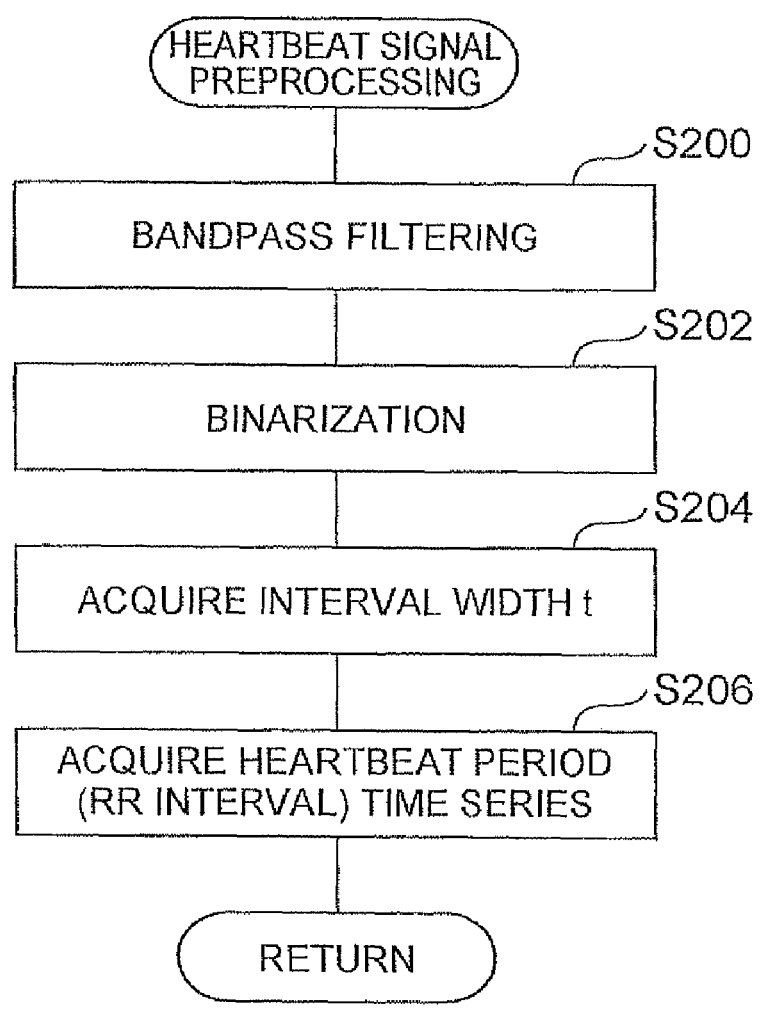
FIG. 3 is a flowchart showing a processing procedure of heartbeat signal preprocessing in FIG. 2.
Figure 4:
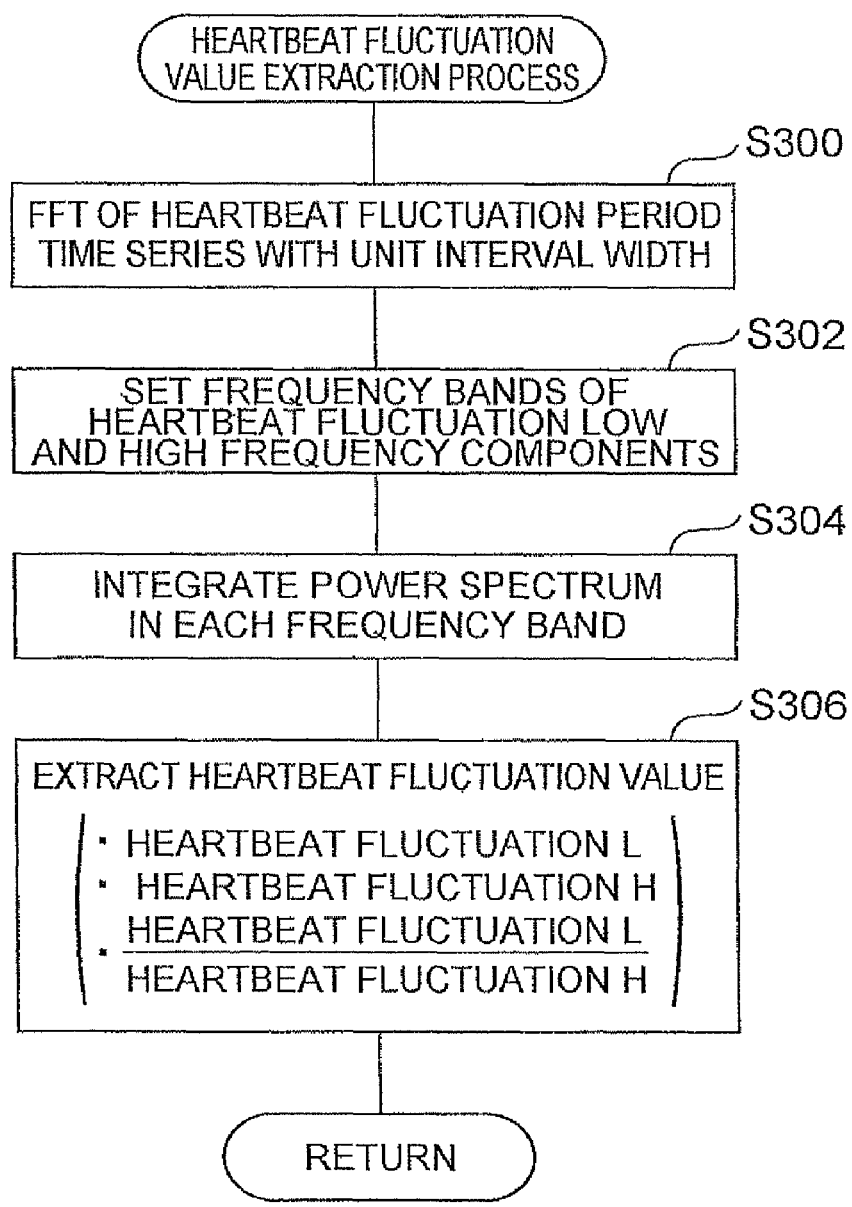
FIG. 4 is a flowchart showing a processing procedure of a heartbeat fluctuation value extraction process in FIG. 2.

With reference to FIG. 1, operations of the dozing occurrence predicting device 1 will be explained. In particular, the processing of the ECU 4 as a whole will be explained along the flowchart of FIG. 2, while the heartbeat signal preprocessing and heartbeat fluctuation value extraction process therein will be explained along the flowcharts of FIGS. 3 and 4, respectively.

At fixed time intervals, the heartbeat sensor 2 detects the cardiac potential of the driver and sends a heartbeat signal to the ECU 4. The ECU 4 reads the heartbeat signal from the heartbeat sensor 2 (S100) and executes the heartbeat signal preprocessing by using a time series of heartbeat signals (S102).

Figure 5:
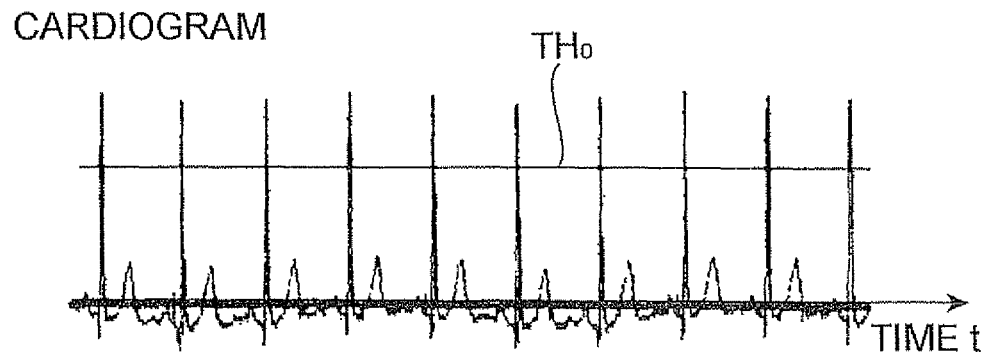
FIG. 5 is a chart showing an example of heartbeat signals.

First, the ECU 4 processes the time-series data of heartbeat signals through a bandpass filter, so as to take out a component of 0.1 Hz to 30 Hz from the time-series data of heartbeat signals (S200). FIG. 5 shows an example of results of processing by bandpass filtering for the cardiac potential.

Figure 6:
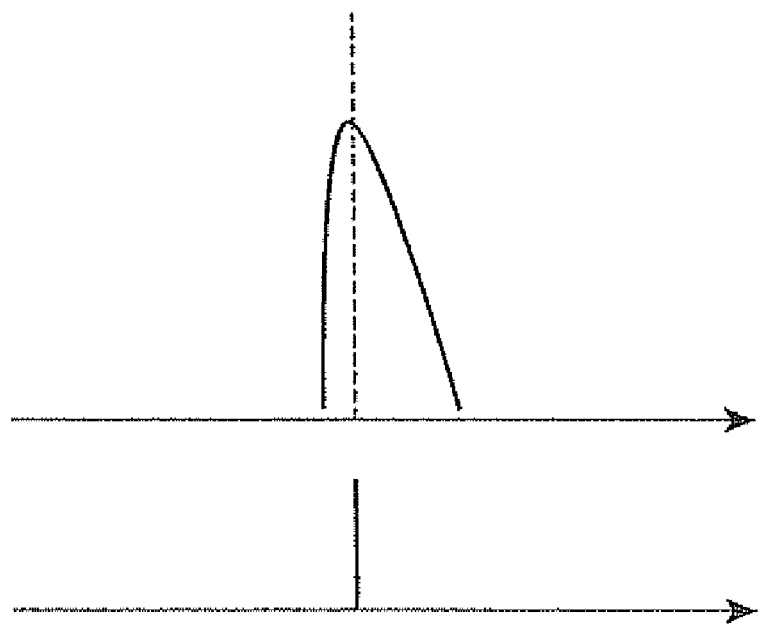
FIG. 6 is a schematic diagram for explaining a binarization process of the heartbeat signal.
Figure 7:
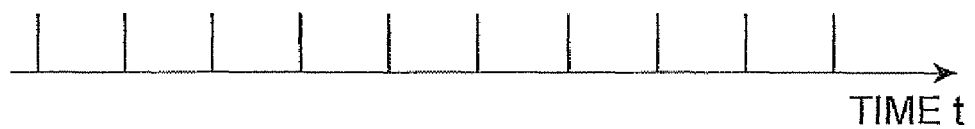
FIG. 7 is a schematic diagram showing a binary signal obtained by binarizing the heartbeat signal.

Subsequently, the ECU 4 cuts out a waveform part which is not lower than a heartbeat timing detecting threshold $TH_0$ from the time-series data of heartbeat signals processed by the bandpass filter (see FIG. 5). Then, as shown in FIG. 6, the ECU 4 binarizes the cut-out data such that timings at which the cut-out waveform part is maximized become 1 while the other timings become 0 (S202). As a consequence, time series data of a series of heartbeat timings are determined as shown in FIG. 7.

Figure 8:
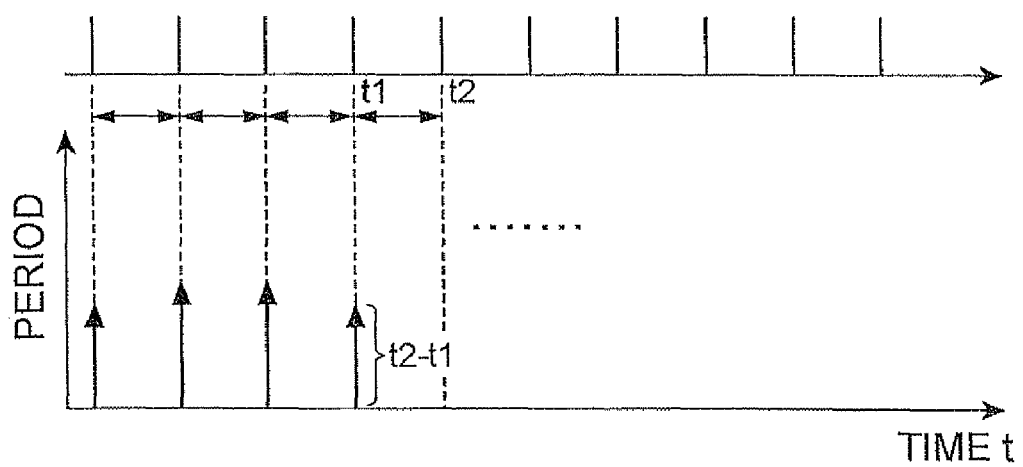
FIG. 8 is a schematic diagram for explaining a process for calculating a heartbeat period.

Next, as shown in FIG. 8, the ECU 4 determines a time (sec) from each heartbeat timing t1 to the next heartbeat timing t2 and imparts thus determined time (=t2−t1) to each heartbeat timing t1 (S204). This yields time-series data of heartbeat period information as shown in FIG. 8.

Figure 9:
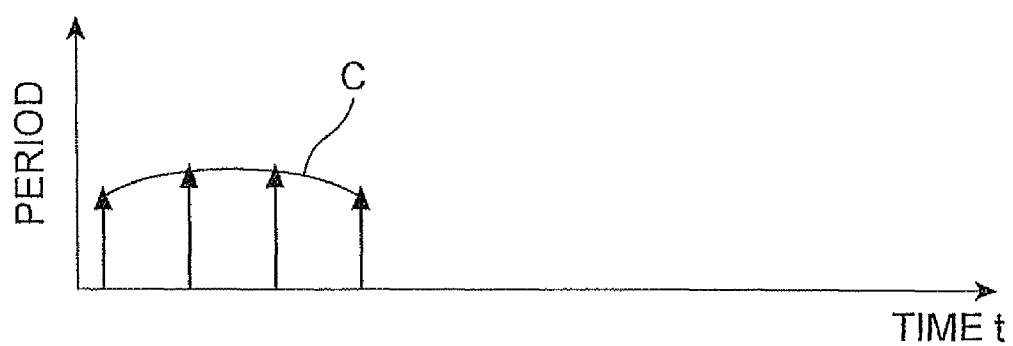
FIG. 9 is a schematic diagram for explaining an interpolation process for the heartbeat period.

Subsequently, as shown in FIG. 9, the ECU 4 interpolates the heartbeat period information (interval width t), so as to determine a heartbeat period curve C (S206). This yields heartbeat period time-series data. Then, the ECU 4 executes a heartbeat fluctuation value extraction process for extracting the heartbeat fluctuations L, H, and L/H from the heartbeat period time-series data (S104).

Figure 10:
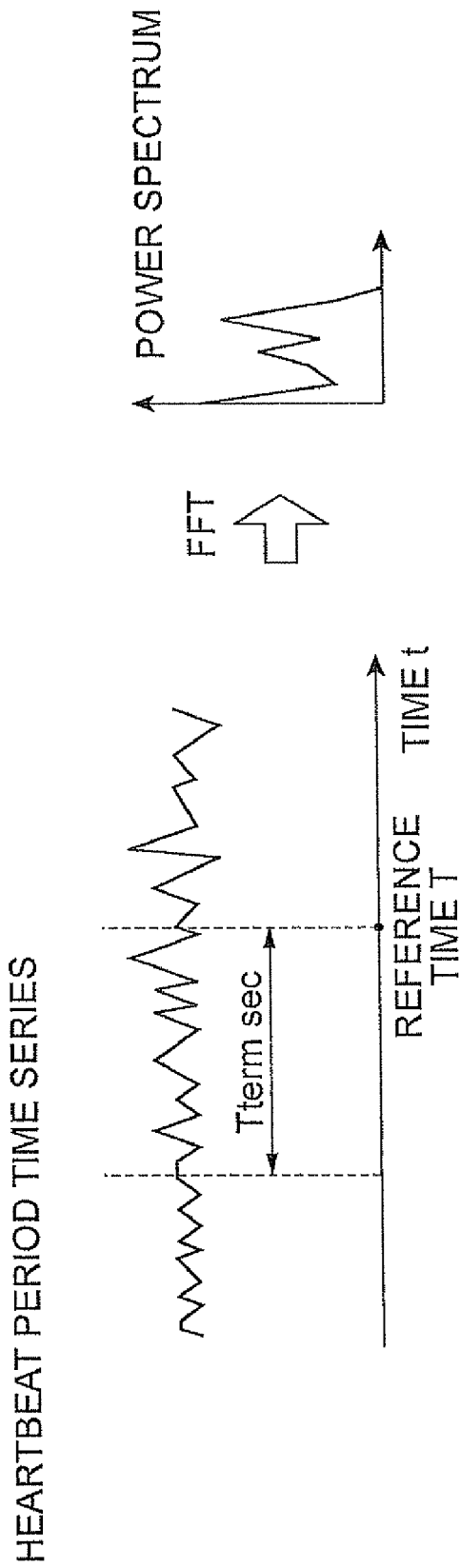
FIG. 10 is a schematic diagram for explaining an FFT process for the heartbeat period.

First, as shown in FIG. 10, the ECU 4 performs fast Fourier transform (FFT) for the heartbeat period time series data in an analysis unit interval width Tterm (sec) prior to a reference time T which is a given timestamp (S300). This yields a power spectrum which is a heartbeat fluctuation frequency component.

Figure 11:
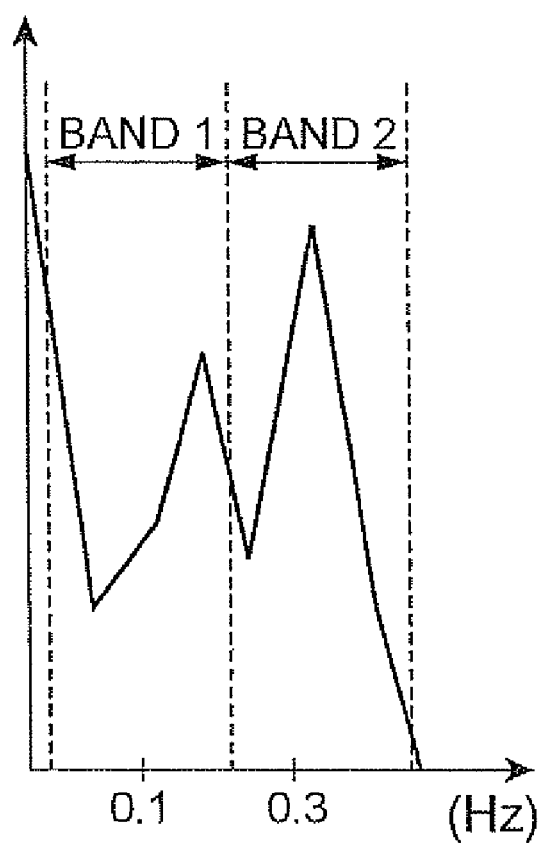
FIG. 11 is a schematic diagram for explaining a frequency band setting for heartbeat fluctuation high and low frequency components.

Next, as shown in FIG. 11, the ECU 4 sets respective frequency bands of the low frequency component (around 0.1 Hz) and high frequency component (around 0.3 Hz) for the power spectrum obtained by the FFT processing in each analysis unit interval (S302). Then, the ECU 4 integrates the power spectrum in each of thus set frequency bands (S304). Further, the ECU 4 divides the integral of the low frequency component band by the integral of the high frequency component band. This yields the heartbeat fluctuation L (low frequency component amplitude spectral power), heartbeat fluctuation H (high frequency component amplitude spectral power), and heartbeat fluctuation L/H (low frequency component/high frequency component amplitude spectral power).

Figure 12:
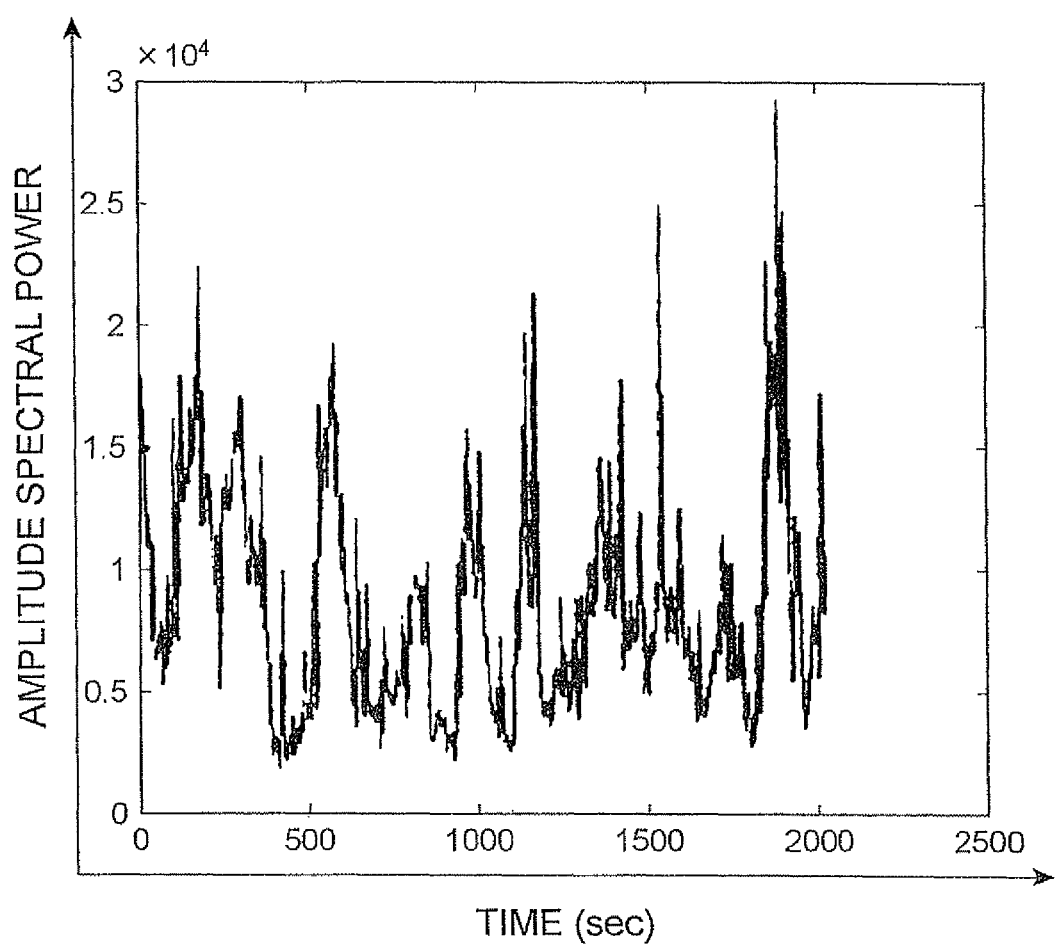
FIG. 12 is a diagram showing an example of changes in amplitude spectral power with time.

Subsequently, at each reference time T after the lapse of a predetermined time, the ECU 4 repeats the above-mentioned processing, so as to acquire heartbeat fluctuation value time-series data (S306). This yields respective time-series data of the heartbeat fluctuations L, H, and L/H. FIG. 12 shows an example of low frequency component amplitude spectral power time-series data.

Each time the heartbeat fluctuation L, H, or L/H is acquired, the ECU 4 stores thus acquired heartbeat fluctuation L, H, or L/H into the heartbeat fluctuation value storage buffer 12 (S106). As a consequence, respective time-series data of the heartbeat fluctuations L, H, and L/H are stored into the heartbeat fluctuation value storage buffer 12.

As shown in FIG. 13, using the time-series data of the heartbeat fluctuation L or L/H, the ECU 4 determines whether the data exceeds the sympathetic activity briskness determining threshold D2 or not, thereby detecting whether the sympathetic activity attains the brisk state or not (S108). After determining that the data exceeded the sympathetic activity briskness determining threshold D2, the ECU 4 counts the duration during which the data exceeds the sympathetic activity briskness determining threshold D2 and determines whether the data fails to exceed the sympathetic activity briskness determining threshold D2 or not, thereby detecting whether the brisk state of the sympathetic activity is subdued or not (S108). When it is determined that the data fails to exceed the sympathetic activity briskness determining threshold D2, the ECU 4 stores the duration DurD2 during which the data exceeded the sympathetic activity briskness determining threshold D2 and the end time TDurD2 of the duration DurD2 (S108). This detects a period in which the sympathetic activity is in a brisk state, and yields the duration DurD2 of the active state and the time TDurD2 at which this state ends.

Then, the ECU 4 determines whether the duration DurD2 exceeds the duration threshold ST or not (i.e., the brisk state of the parasympathetic activity is kept sufficiently or not) (S110). When it is determined at S110 that the duration DurD2 exceeded the duration threshold ST, the ECU 4 stores the time TDurD2 into the sympathetic activity brisk time storage buffer 15 (S112). This determines whether or not the brisk state of the sympathetic activity is kept enough to predict the occurrence of the dozing state. When the brisk state is kept sufficiently, the time TDurD2 at which the brisk state ends is obtained. When it is determined at S110 that the duration DurD2 fails to exceed the duration threshold ST, on the other hand, the ECU 4 repeats the processing from S100.

Figure 14:
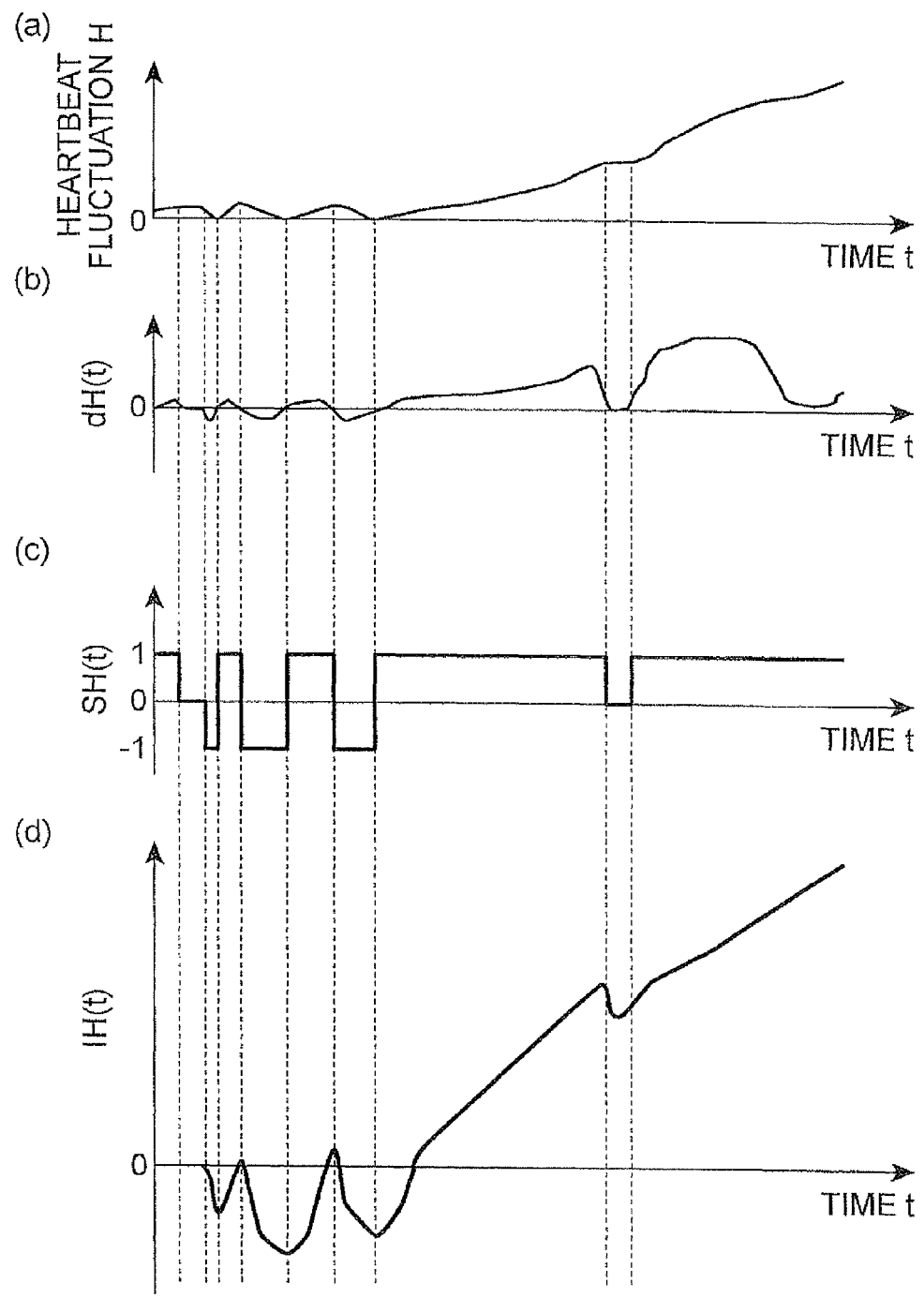
FIG. 14 is a schematic diagram for explaining the parasympathetic activity briskness detecting process, in which (a) is a time series of a heartbeat fluctuation H, (b) is a time series of the derivative dH(t) of the heartbeat fluctuation H, (c) is a time series of the sign SH(t) of the derivative dH(t), and (d) is a time series of the time integral IH(t) of the sign SH(t)

As shown in FIG. 14, the ECU 4 differentiates the time-series data of heartbeat fluctuation H with respect to time, encodes the resulting derivative dH(t) by expression (1), and integrates the resulting derivative sign SH(t) with respect to time by expression (2), thereby generating time-series data of the sign integral IH(t) (S114). As the value of sign integral IH(t) is positively greater, it indicates that the brisk state of the parasympathetic activity is kept more, whereby the brisk state of the parasympathetic activity and its state of continuation can be detected from the sign integral IH(t).

Figure 15:
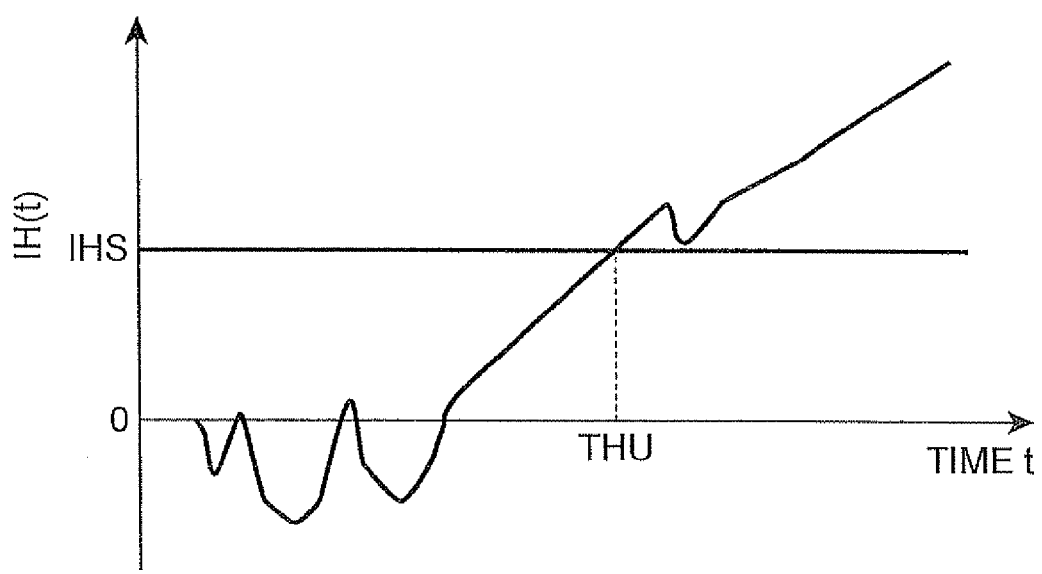
FIG. 15 is a schematic diagram for explaining the parasympathetic activity briskness detecting process.

As shown in FIG. 15, the ECU 4 determines whether the sign integral IH(t) exceeds the parasympathetic activity briskness determining threshold IHS or not (i.e., whether the parasympathetic activity is in the brisk state or not) (S116). When it is determined at S116 that the integral exceeded the parasympathetic activity briskness determining threshold IHS, the ECU 4 stores the time THU at which the integral exceeded the threshold into the parasympathetic activity brisk time storage buffer 18 (S118). As a consequence, it is determined that the parasympathetic activity is brisk enough to predict the occurrence of the dozing state, and the time THU at which this determination is made is obtained. When it is determined at S116 that the integral fails to exceed the parasympathetic activity briskness determining threshold IHS, on the other hand, the ECU 4 repeats the processing from S100.

When both of the sympathetic activity brisk state end time TDurD2 and the parasympathetic activity brisk state start time THU are buffered, the ECU 4 determines whether or not the time THU is later than the time TDurD2 while (THU−TDurD2)<the shift time threshold TSleep, thereby determining the prediction of the occurrence of the dozing state (S120). When the determining condition of S120 is not satisfied, the ECU 4 predicts that the dozing state will not occur, and repeats the processing from S100.

When the determining condition of S120 is satisfied, on the other hand, the ECU 4 determines that the weak drowsiness has shifted to the strong drowsiness, predicts that the dozing state will occur, and sends an output signal for notifying the result of determination to the output means 3 (S122). Upon receiving the output signal, the output means 3 issues an output for reporting that the driver is in the strongly drowsy state, which will immediately become the dozing state. This output makes the driver notice the approaching of the dozing state or causes people other than the driver to recognize that the driver is getting into the dozing state and alert the driver. This weakens the drowsiness of the driver or makes the driver take a rest.

As an evaluation test for the dozing occurrence predicting device 1, a test for determining the strongly drowsy state to become the dozing state was conducted. Here, results of determination of strong drowsiness based on heartbeat fluctuation values of a subject (driver) and results of sensory evaluations obtained from face images of the subject were compared with each other, so as to perform the evaluation test. The method and results of the test will be explained.

The test was carried out in the following procedure. 1. Acquire a face image time series of a subject simultaneously with measurement of a heartbeat signal of the subject. 2. Evaluate the face image time series with reference to the following levels 1 to 5 and classify the drowsiness of the subject into 5-stage levels. Here, evaluators for the sensory evaluation are plural (e.g., two). 3. Compute an average value Sens (sensory evaluation level) of sensory evaluations by the plurality of evaluators. 4. Acquire drowsiness levels D0 to D4 based on the sensory evaluation from the sensory evaluation average value Sens according to the table shown in FIG. 19. 5. Simultaneously determine the strong drowsiness of the subject by the dozing occurrence predicting device 1 according to the heartbeat fluctuation value obtained from a time series of heartbeat signals. For fairness of evaluation, the evaluators had not been provided with information about the heartbeat fluctuation value of the subject at all.

The sensory evaluation levels will now be explained. Level 1 is not sleepy at all (the line of sight moves fast and frequently; blinking has a stable period of about 2 per 2 sec; movement is brisk with body actions). Level 2 is somewhat sleepy (lips are open; the line of sight moves slowly). Level 3 is sleepy (blinking is slowly and frequently; mouth moves; reseating; touching the face with a hand). Level 4 is fairly sleepy (blinking which seems to be intentional; unnecessary whole body actions such as shaking the head and moving the shoulder up and down; frequent yawning; deep breathing; blinking and movement of line of sight are slow). Level 5 is very sleepy (eyelids are closed; the head tilts forward; the head falls backward). (Ref: "Human Sensory Measurement Manual, Vol. 1", p. 146, Research Institute of Human Engineering for Quality Life)

Figure 16:
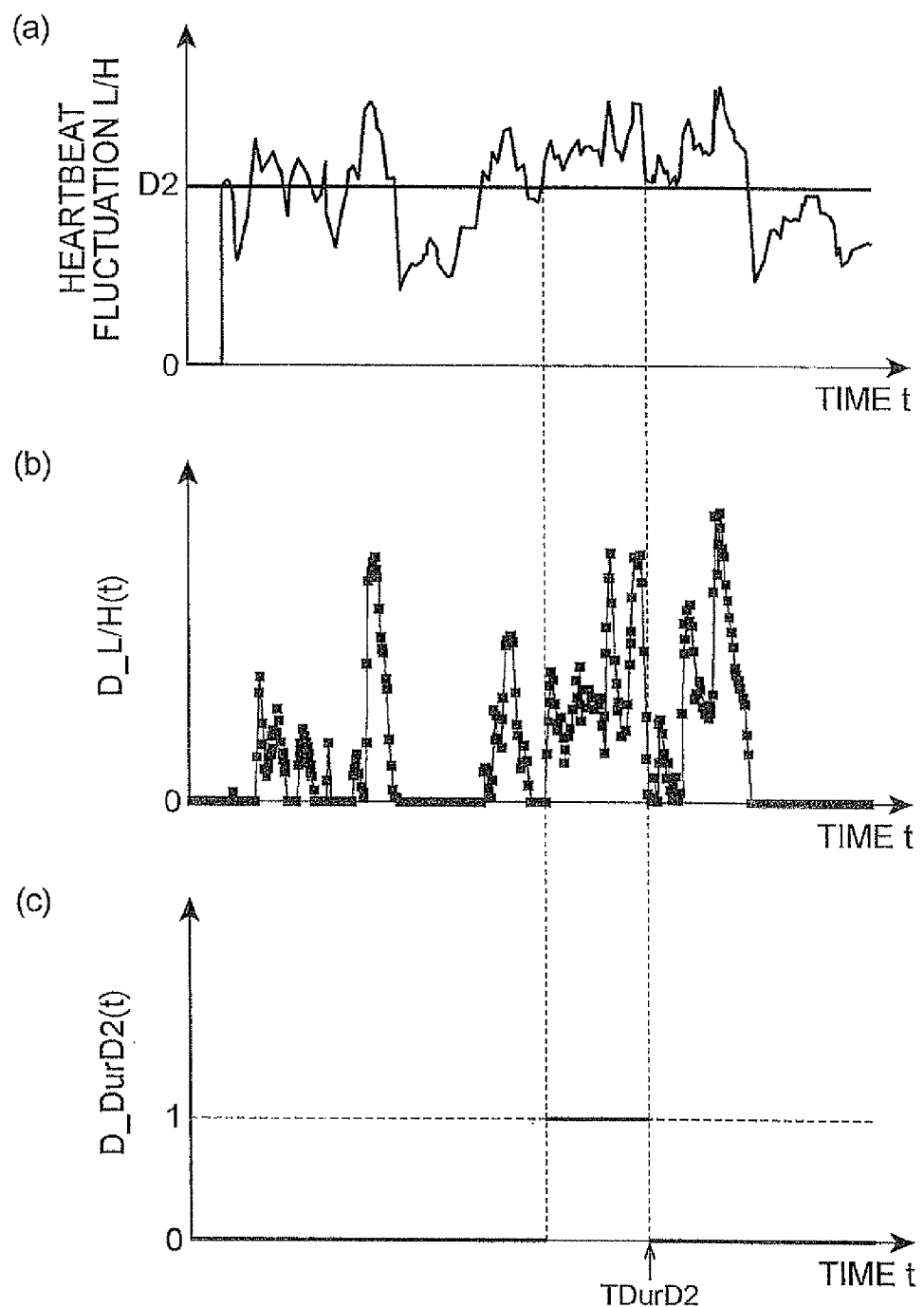
FIG. 16 is an example of evaluation tests for the dozing occurrence predicting device, in which (a) is a time series of a heartbeat fluctuation L/H, (b) is a time series of a component D_L/H(t) after processing the heartbeat fluctuation L/H with a sympathetic activity briskness determining threshold D2, and (c) is a time series of an interval D_DurD2($t$) after processing the D_L/H(t) with a duration threshold ST.
Figure 18:
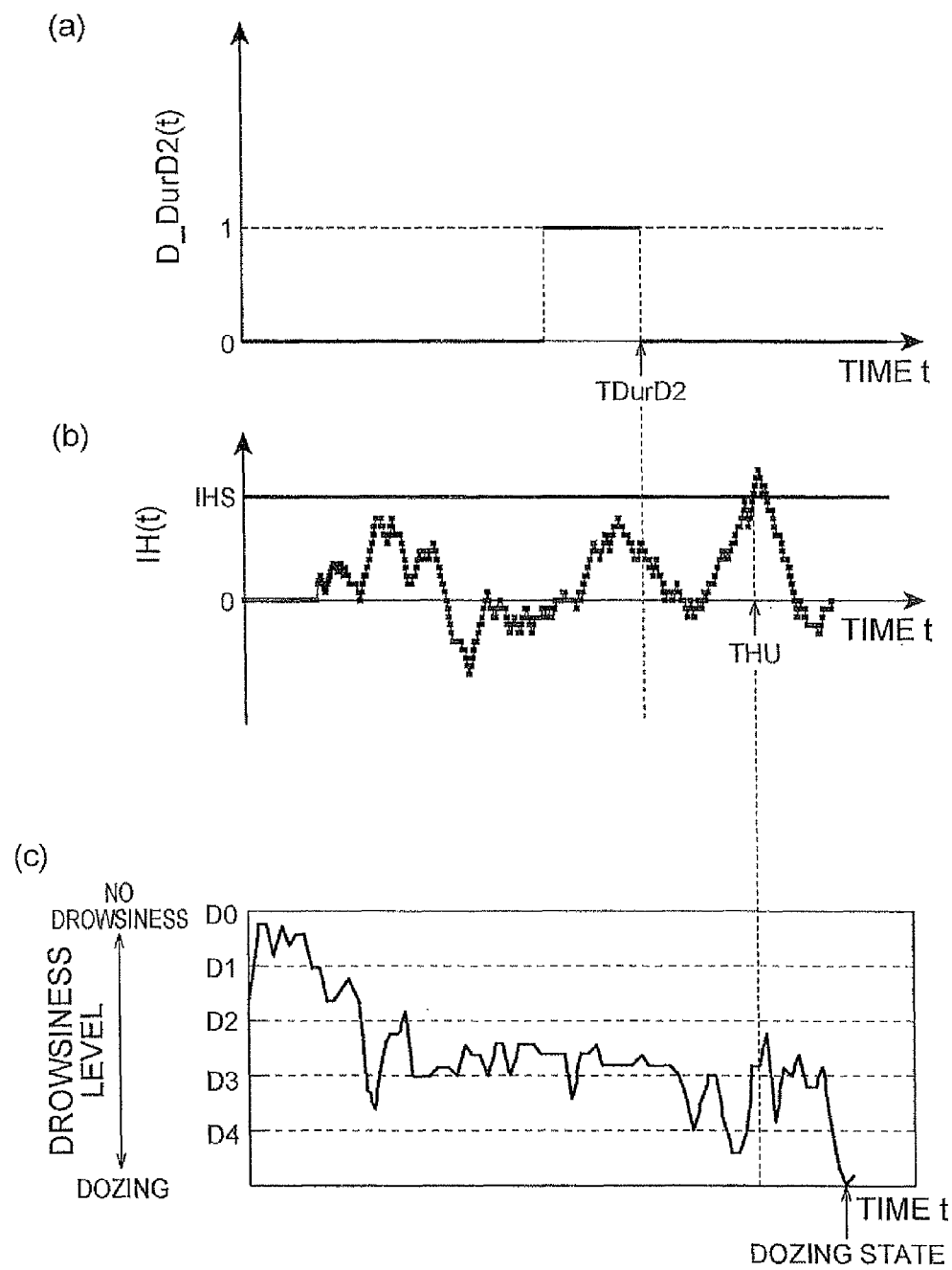
FIG. 18 is an example of evaluation tests for the dozing occurrence predicting device, in which (a) is a time series of the D_DurD2($t$) in FIG. 16($c$), ($b$) is a time series of the sign integral IH(t) with the parasympathetic activity briskness determining threshold IHS in FIG. 17(c), and (c) is a time series of drowsiness levels by sensory evaluations.

FIGS. 16 to 18 show an example of the evaluation test for the dozing occurrence predicting device 1. FIG. 16 shows data handled by the sympathetic activity briskness detection processing section 13 and the sympathetic activity briskness detection determining section 14, FIG. 17 shows data handled by the parasympathetic activity briskness detection processing section 16 and the parasympathetic activity briskness detection determining section 17, and FIG. 19 shows data handled by the dozing occurrence predicting section 19.

FIG. 16(*a*) shows time-series data of the heartbeat fluctuation L/H, which includes an interval where the heartbeat fluctuation L/H exceeds the sympathetic activity briskness determining threshold D2. FIG. 16(*b*) shows time-series data of the part D_L/H(t) exceeding the sympathetic activity briskness determining threshold D2 in the heartbeat fluctuation L/H in FIG. 16(*a*). FIG. 16(*c*) shows time-series data of D_DurD2(*t*) in which intervals greater than 0 whose durations exceed the duration threshold ST and not are taken as 1 and 0, respectively. The interval yielding 1 in the time-series data of D_DurD2(*t*) is an interval where the brisk state of the sympathetic activity is kept sufficiently, whereas the brisk interval ends at the time TDurD2.

FIG. 17(*a*) shows time-series data of the heartbeat fluctuation H. FIG. 17(*b*) shows time-series data of the sign integral IH(t) obtained from the time-series data of the heartbeat fluctuation H in FIG. 17(*a*). FIG. 17(*c*) shows the sign integral IH(t) and parasympathetic activity briskness determining threshold IHS together with the time THU at which the sign integral IH(t) exceeds the parasympathetic activity briskness determining threshold IHS. At the time THU, the parasympathetic activity is in a sufficiently brisk state.

FIG. 18(*a*) shows time-series data of D_DurD2(*t*) in FIG. 16(*a*) with the time TDurD2 at the end of the interval of 1 (i.e., the time at which it is determined that the brisk state of the sympathetic activity ends). FIG. 18(*b*) shows time-series data of IH(t) in FIG. 17(*c*) with the time THU at which the parasympathetic activity briskness determining threshold IHS is exceeded (i.e., the time at which the parasympathetic activity is determined to be in the brisk state). FIG. 18(*c*) shows time-series data of drowsiness levels by the sensory evaluation.

FIGS. 18(*a*), 18(*b*), and 18(*c*) are aligned in terms of the time axis, so that the time THU comes after the time TDurD2, while their time difference (THU−TDurD2) is shorter than the shift time threshold TSleep. Therefore, at the time THU, the dozing occurrence predicting device 1 determines the strongly drowsy state to become the dozing state. At the time THU, the drowsiness level was D3, where the subject was in a fairy sleepy state and attained the dozing state immediately thereafter. Thus, the dozing occurrence predicting device 1 succeeded in detecting the strongly drowsy state of the subject (predicting the occurrence of the dozing state), whereby the effectiveness of the dozing occurrence predicting device 1 has been verified.

From the increase/decrease phase relationship between the sympathetic and parasympathetic activities based on heartbeat fluctuation values, this dozing occurrence predicting device 1 can predict the occurrence of the drowsy state several to ten-odd minutes therebefore with a high accuracy (i.e., can determine the strong drowsiness before the occurrence of the dozing state with a high accuracy). Therefore, the driver can be alerted at an optimal timing before getting into the dozing state, so that the degree of awakening of the driver can be raised or the driver can be urged to take a rest before driving operations are affected.

The dozing occurrence predicting device 1 determines the brisk states of sympathetic and parasympathetic activities in terms of absolute values according to the thresholds each set for all the people, and thus can predict the occurrence of the dozing state with a higher accuracy. In the case of determination by relative values which vary among individuals, the drowsiness is determined according to a relative change from a heartbeat fluctuation value at the time of starting driving (where the degree of awakening is predicted to be high) taken as a reference value, for example, whereby the accuracy of determination will lower if the drowsiness exists at the time of starting driving.

The dozing occurrence predicting device 1 introduces the concept of time when determining the brisk states of sympathetic and parasympathetic activities, and thus can determine the active states with a higher accuracy. Also, the dozing occurrence predicting device 1 simply sees only the increase/decrease direction (sign) of the heartbeat fluctuation H and its increase/decrease time when determining the brisk state of the parasympathetic activity, and thus can absorb individual differences, thereby making it possible to determine the brisk state of the parasympathetic activity with a higher accuracy.

Though an embodiment in accordance with the present invention has been explained in the foregoing, the present invention can be carried out in various modes without being restricted to the above-mentioned embodiment.

For example, the present invention is employed for a dozing occurrence predicting device for predicting the occurrence of dozing in the driver of a vehicle in this embodiment, but may be utilized for predicting the occurrence of dozing in various people such as drivers of other carriers, surveyors of various plants, and night workers and employed in drowsiness detecting devices for determining drowsiness levels (D3, D4) such as the strong drowsiness to become dozing.

Though this embodiment is constructed so as to detect the sympathetic and parasympathetic activities by utilizing heartbeats, other indexes such as aspirations may be used for detecting the sympathetic and parasympathetic activities.

Though this embodiment is constructed such as to determine the strongly drowsy state in the case where the sympathetic activity attains the brisk state and then the parasympathetic activity becomes the brisk state after the brisk state of the sympathetic activity is subdued, the strongly drowsy state may be determined in the case where the sympathetic activity attains the brisk state and then the parasympathetic activity becomes the brisk state while the sympathetic activity keeps its brisk state.

Though this embodiment has set forth an example as the method of determining the brisk state of the sympathetic activity and determining the brisk state of the sympathetic activity, various methods can be employed without being restricted thereto.

Though this embodiment is constructed such as to notify a result of determination when the strong drowsiness is determined, an action for raising the degree of awakening such as imparting a stimulus to the driver may be taken when the strong drowsiness is determined.

INDUSTRIAL APPLICABILITY

The drowsiness determining device in accordance with the present invention can determine the strong drowsiness to become the dozing state with a high accuracy by determining the increase/decrease relationship between the sympathetic and parasympathetic activities.

The invention claimed is:

1. A drowsiness determining device comprising:
a sympathetic parameter acquiring unit for acquiring a parameter concerning a sympathetic nerve of a subject;
a parasympathetic parameter acquiring unit for acquiring a parameter concerning a parasympathetic nerve of the subject;
a sympathetic increase determining unit for determining whether the sympathetic parameter acquired by the sympathetic parameter acquiring unit is greater than a sympathetic threshold or not, wherein the sympathetic increase determining unit determines that the sympathetic parameter is greater than the sympathetic threshold when a duration during which the sympathetic parameter acquired by the sympathetic parameter acquiring unit is greater than the sympathetic threshold is longer than a time threshold; and
a drowsiness determining unit for determining drowsiness of the subject according to an increase/decrease relationship between the sympathetic parameter acquired by the sympathetic parameter acquiring unit and the parasympathetic parameter acquired by the parasympathetic parameter acquiring unit when the sympathetic increase determining unit determines that the sympathetic parameter is greater than the sympathetic threshold.

2. The drowsiness determining device according to claim 1, wherein the parasympathetic parameter acquiring unit acquires the parasympathetic parameter according to an increase/decrease direction of a heartbeat fluctuation high frequency component.

3. The drowsiness determining device according to claim 1, further comprising a parasympathetic increase determining unit for determining whether the parasympathetic parameter acquired by the parasympathetic parameter acquiring unit is greater than a parasympathetic threshold or not;
wherein the drowsiness determining unit determines that the subject is in a strongly drowsy state when the parasympathetic increase determining unit determines that the parasympathetic parameter is greater than the parasympathetic threshold after the sympathetic increase determining unit determines that the sympathetic parameter is smaller than the sympathetic threshold in a case where the sympathetic increase determining unit determines that the sympathetic parameter is greater than the sympathetic threshold.

4. The drowsiness determining device according to claim 1, further comprising a parasympathetic increase determining unit for determining whether the parasympathetic parameter acquired by the parasympathetic parameter acquiring unit is greater than a parasympathetic threshold or not;
wherein the drowsiness determining unit determines that the subject is in a strongly drowsy state when the parasympathetic increase determining unit determines that the parasympathetic parameter is greater than the parasympathetic threshold while the sympathetic increase determining unit keeps determining that the sympathetic parameter is greater than the sympathetic threshold in a case where the sympathetic increase determining unit determines that the sympathetic parameter is greater than the sympathetic threshold.

* * * * *